United States Patent
Besselink et al.

(10) Patent No.: US 7,204,818 B2
(45) Date of Patent: Apr. 17, 2007

(54) PROSTHESIS OR ORTHESIS WITH REDUCED CONTACT FRICTION

(75) Inventors: Mark Stefan Besselink, Enschede (NL); Nicolaas Gerardus Adrianus Van Leerdam, Hengelo (NL); Jurrie Van Der Woude, Almelo (NL)

(73) Assignee: Kunst & Van Leerdam IP B.V., Enschede (NL)

( * ) Notice: Subject to any disclaimer, the term of this patent is extended or adjusted under 35 U.S.C. 154(b) by 0 days.

(21) Appl. No.: 10/516,798

(22) PCT Filed: Jun. 5, 2003

(86) PCT No.: PCT/NL03/00414
§ 371 (c)(1),
(2), (4) Date: Jul. 21, 2005

(87) PCT Pub. No.: WO03/103546

PCT Pub. Date: Dec. 18, 2003

(65) Prior Publication Data

US 2006/0015047 A1    Jan. 19, 2006

(30) Foreign Application Priority Data

Jun. 6, 2002    (NL)    ................................... 1020776

(51) Int. Cl.
*A61F 5/00*    (2006.01)
(52) U.S. Cl. .............................. 602/16; 602/5; 602/23; 602/26
(58) Field of Classification Search ............. 602/5, 602/16, 23, 62, 65, 26, 27; 601/122, 123, 601/124, 125, 131, 132
See application file for complete search history.

(56) References Cited

U.S. PATENT DOCUMENTS

| 1,099,938 | A | | 6/1914 | Rowley |
| 3,732,578 | A | | 5/1973 | Pollack |
| 4,506,661 | A | | 3/1985 | Foster |
| 4,957,442 | A | | 9/1990 | Prater |
| 5,019,064 | A | | 5/1991 | Eilender |
| 5,085,210 | A | | 2/1992 | Smith, III |
| 5,464,443 | A | | 11/1995 | Wilson et al. |
| 5,641,322 | A | | 6/1997 | Silver et al. |
| 6,362,387 | B1 | | 3/2002 | Carlson et al. |
| 6,960,175 | B1 | * | 11/2005 | Myers ......................... 602/16 |
| D521,644 | S | * | 5/2006 | Nordt et al. ............... D24/190 |

FOREIGN PATENT DOCUMENTS

WO    WO 97/20527    6/1997

* cited by examiner

*Primary Examiner*—Patricia Bianco
*Assistant Examiner*—Camtu Nguyen
(74) *Attorney, Agent, or Firm*—The Webb Law Firm

(57) ABSTRACT

An orthopedic device comprises: a structure comprising two substantially rigid parts, for instance two rods, which parts are coupled to each other by means of hinge means and each comprise fastening means for optional temporary fastening to a limb part, wherein a pivot axis of the hinge means extends at least more or less in the region and in the direction of the pivot axis zone of the relevant joint. The device has the feature according to the invention that the fastening means are at least partly provided with friction-reducing means on at least the side to be brought into contact with the relevant limb part.

7 Claims, 5 Drawing Sheets

PROSTHESIS OR ORTHESIS WITH REDUCED CONTACT FRICTION

BACKGROUND OF THE INVENTION

The invention relates to an orthopaedic device, in particular a prosthesis or an orthosis, for the purpose of replacing respectively supporting the function of at least one part of a human limb with a pivotable joint, for example a leg with a knee or an arm with an elbow, on either side of which joint there extend respective limb parts, such as a lower leg and an upper leg respectively a lower arm and an upper arm, which device comprises:

a structure comprising two substantially rigid parts, for instance two rods, which parts are coupled to each other by means of hinge means and each comprise fastening means for optional temporary fastening to a limb part, wherein a pivot axis of the hinge means extends at least more or less in the region and in the direction of the pivot axis zone of the relevant joint.

An orthosis is an assist means for supporting a limb with a reduced functionality and can be applied for instance with a paralysed leg. Said rigid parts of the stated structure are fastened releasably by means of fastening means to the relevant limb parts on either side of the joint in question, for example lower leg and upper leg and the knee connecting these two parts.

For the best possible operation the device must be placed in the correct manner relative to the limb parts. The centre line of a knee hinge of a knee orthosis must for instance correspond as well as possible to the movement axis of the knee.

There are a number of reasons why an orthopaedic device of the present type does not remain in place. The movement of skin and limb parts and the weight of the device are causes, among others, of shifting displacements.

The weight of the device will generally cause it to want to slip downward.

Through the relative movements of the limb parts one or more joints and, in the case of an orthosis, hinge means will bend and straighten. Since hinge parts do not have exactly the same movement characteristics as joints, a shifting displacement of the device takes place, the movement of which is imparted by the hinge means, relative to the limb part in question, the movement of which is imparted by the joint. In the case of for instance a knee orthosis, this shifting displacement can amount to several centimeters. This shifting displacement must be impeded as little as possible by fastening means, since otherwise the movement of the joint would be obstructed thereby. The movement of the elastic skin occurs mainly during movement of the joints. A known problem in known devices with usual fastening means which are substantially immovable relative to the limb parts is that the device co-displaces with the stretching skin, but does not move back again with the skin as it moves back. This causes a shifting displacement of the device.

A distinction has to be made between desired and undesired shifting displacements of the device in relation to the body. As mentioned above, a desired shifting displacement is one which occurs as a result of the movement of joints. Undesired shifting displacements usually occur under the influence of friction due to stretching skin and due to the weight of the device.

Devices of the type stated in the preamble are known from, among others, WO-A-97/20527, U.S. Pat. No. 5,641,322, U.S. Pat. No. 5,085,210 and U.S. Pat. No. 4,506,661. Devices known from the prior art generally prevent shifting displacement of the device relative to the body part in question or the joints by making use of fastening means which fulfil their function either by making the friction as great as possible between the device including the fastening means on the one hand and the relevant limb part on the other, or by having the device support on body structures which are present, such as bone and/or muscle belly. Particular reference is made in this respect to WO-A-97/20527.

A drawback of such known devices with associated fastening means is their dependence on the co-efficient of friction between the body and the fastening means, or the presence of usable body structures. The co-efficient of friction can vary greatly as a result of for instance perspiration. In order to ensure a minimal friction a high level of bias is therefore generally applied, in other words the fastening means are tied tightly around the relevant limb part. In addition, body structures display great differences from person to person and can also change during use, for example through muscle movements, whereby it is difficult to predict the degree of usefulness thereof as support point.

Another drawback is that the known devices with associated fastening means do not generally make it possible, or hardly so, for the device to displace relative to the body during the combined bending and straightening again of joints and hinge means.

With reference to the above description of the prior art, comfort as well as functional characteristics can also be mentioned as drawbacks of the devices, both of these leaving much to be desired and being capable of improvement.

SUMMARY OF THE INVENTION

In respect of the above the invention provides an orthopaedic device of the type stated in the preamble which has the feature that the fastening means are at least partly provided with friction-reducing means on at least the side to be brought into contact with the relevant limb part.

With the device according to the invention the skin can move as freely as possible and the friction forces can be so small that they will cause no, or the least possible undesired shifting displacement of the device relative to the relevant limb parts or the joints, but that the desired displacement as a result of bending and straightening of the joints and hinge means is also possible. A desired flexible movement is hereby always possible.

A simple embodiment of the device according to the invention has the feature that the friction-reducing means comprise at least one flexible pillow filled with a viscous liquid, for example a gel.

In another embodiment the device has the special feature that the friction-reducing means comprise a layer of suitable plastic, for instance PE (polyethylene) or PTFE (polytetrafluoroethylene).

In yet another embodiment the device has the feature that the friction-reducing means comprise a number of freely rotatable elements, such as rollers or balls.

The orthoses known from the cited publications have a hinge part on either side of the relevant joint. Such orthoses can also be referred to as double-sided orthoses. According to the invention the device can advantageously have the feature that said structure is provided on only one side with hinge means. Better cosmetic results are possible with such a device, which is found to be greatly valued by users during tests.

So as to ensure the best possible fastening while retaining the desired freedom of movement, a device of the described type can have the feature that the fastening means comprise divisible flexible rings with adjustable periphery.

This variant can for instance be embodied with at least one additional ring with adjustable periphery, which ring is connected or can be connected to a structural part and is free of friction-reducing means. The connection must preferably be located at only one position.

A preferred embodiment has the feature that the additional ring is coupled or can be coupled to a ring provided with friction-reducing means by means of an optionally adjustable tensioner extending in longitudinal direction, for example a cord, a draw spring or an elastic strap.

Two applications of the device according to the invention can be pointed to as important embodiments. In the one embodiment the device has the special feature that the device is a knee orthosis. In the other embodiment the device has the special feature that the device is a knee-ankle-foot orthosis.

The invention will now be elucidated on the basis of the annexed drawings of several random embodiments. In the drawings:

DETAILED DESCRIPTION OF THE PREFERRED EMBODIMENTS

Figure 1:
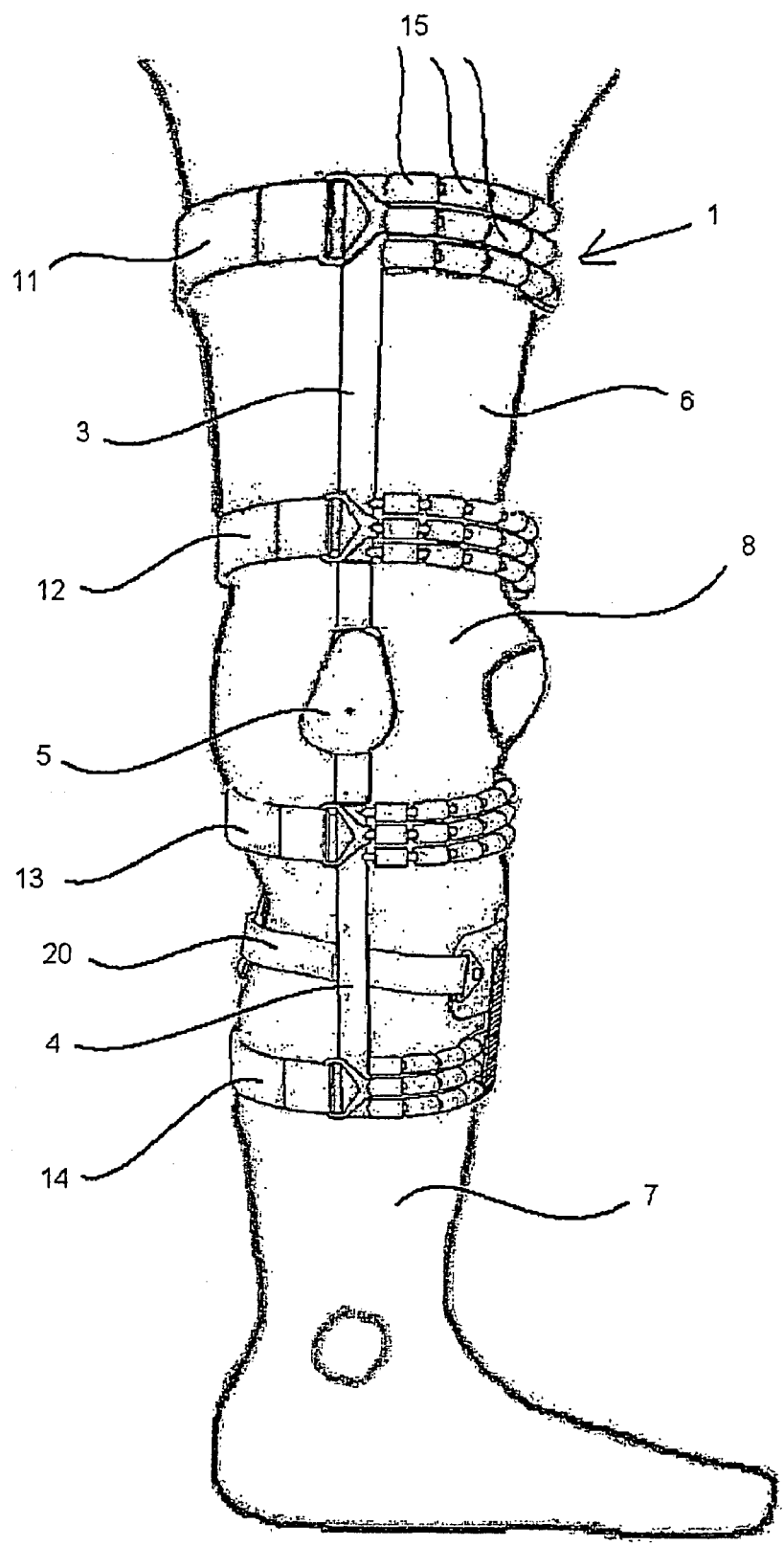
FIG. 1 shows a schematic perspective side view of a leg with an orthosis according to the invention in the straightened position.
Figure 2:
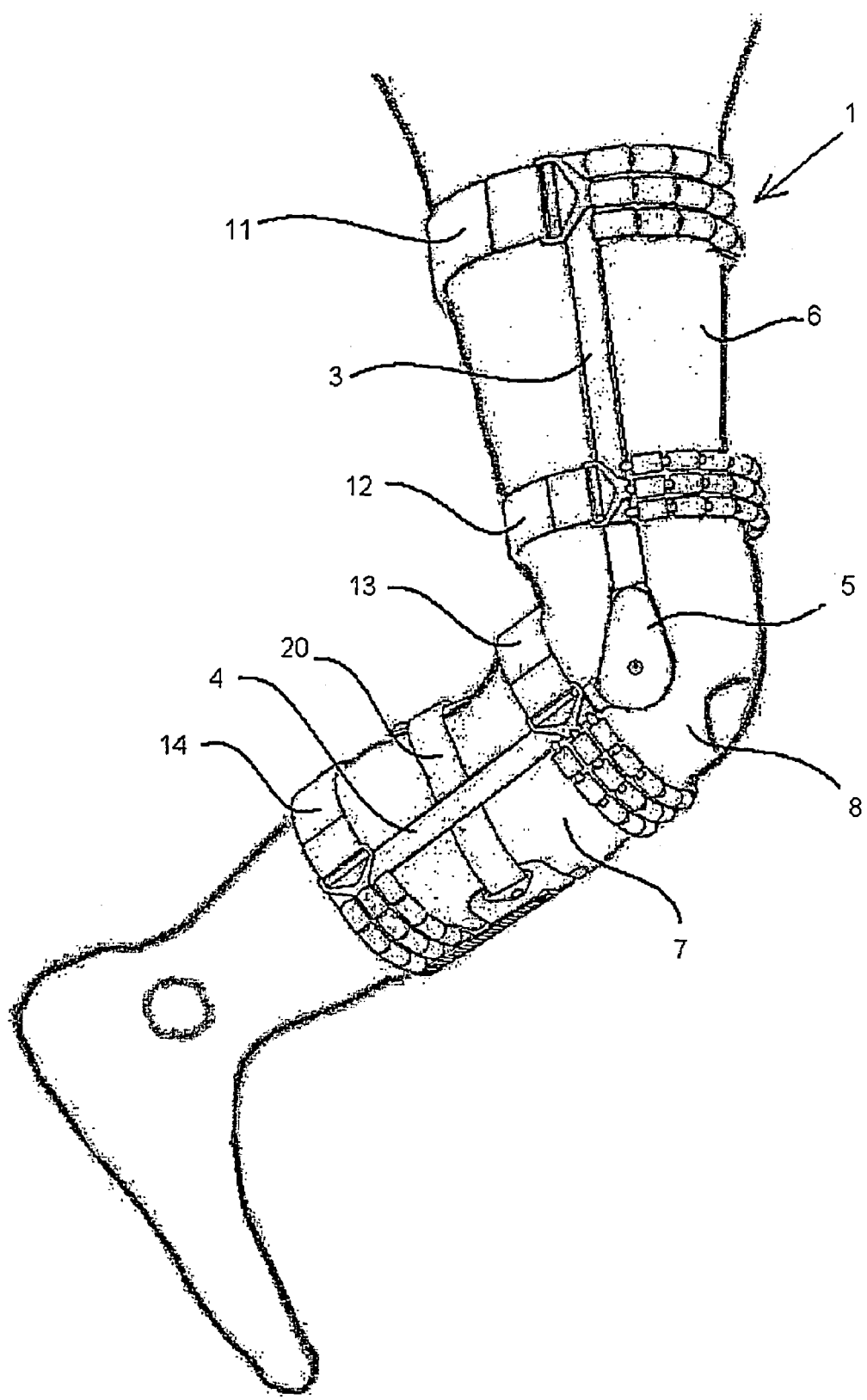
FIG. 2 shows a view corresponding with FIG. 1 of the situation in which the leg is bent.

FIG. 1, 2, 3 show an orthosis 1 according to the invention. The orthosis comprises two rods 3, 4 which are coupled to each other by means of a hinge 5 and co-act with respectively the upper leg 6 and the lower leg 7 of a user. The pivot axis of hinge 5 corresponds substantially with the pivot axis of knee 8. It is noted here that this axis does not have a fixed position and angular position, but that it depends on the relative pivoting position of upper leg 6 and lower leg 7. Fastening rings 11, 12 respectively 13, 14 are connected to rods 3, 4. These rings have an adjustable periphery in per se known manner, for instance by making use of buckle means or Velcro connections.

According to the invention all four fastening rings 11, 12, 13, 14 are provided with means which reduce the friction with the skin. In this embodiment the friction-reducing means comprise a number of freely rotatable rollers, which for the sake of convenience are all designated with 15. These rollers are for example of nylon and are rotatable around for example steel or nylon cords or thin flexible rods 16. In the drawn embodiment of a single-sided orthosis use is made of stiff, form-retaining rods, for instance of stainless steel. In a double-sided orthosis use can be made of nylon cords or thin, at least slightly flexible rods. In this embodiment the rods are connected at their ends to the rear sides of rings 11, 12, 13, 14, and are connected to each other locally, for example in the middle, in at least one location.

Figure 3:
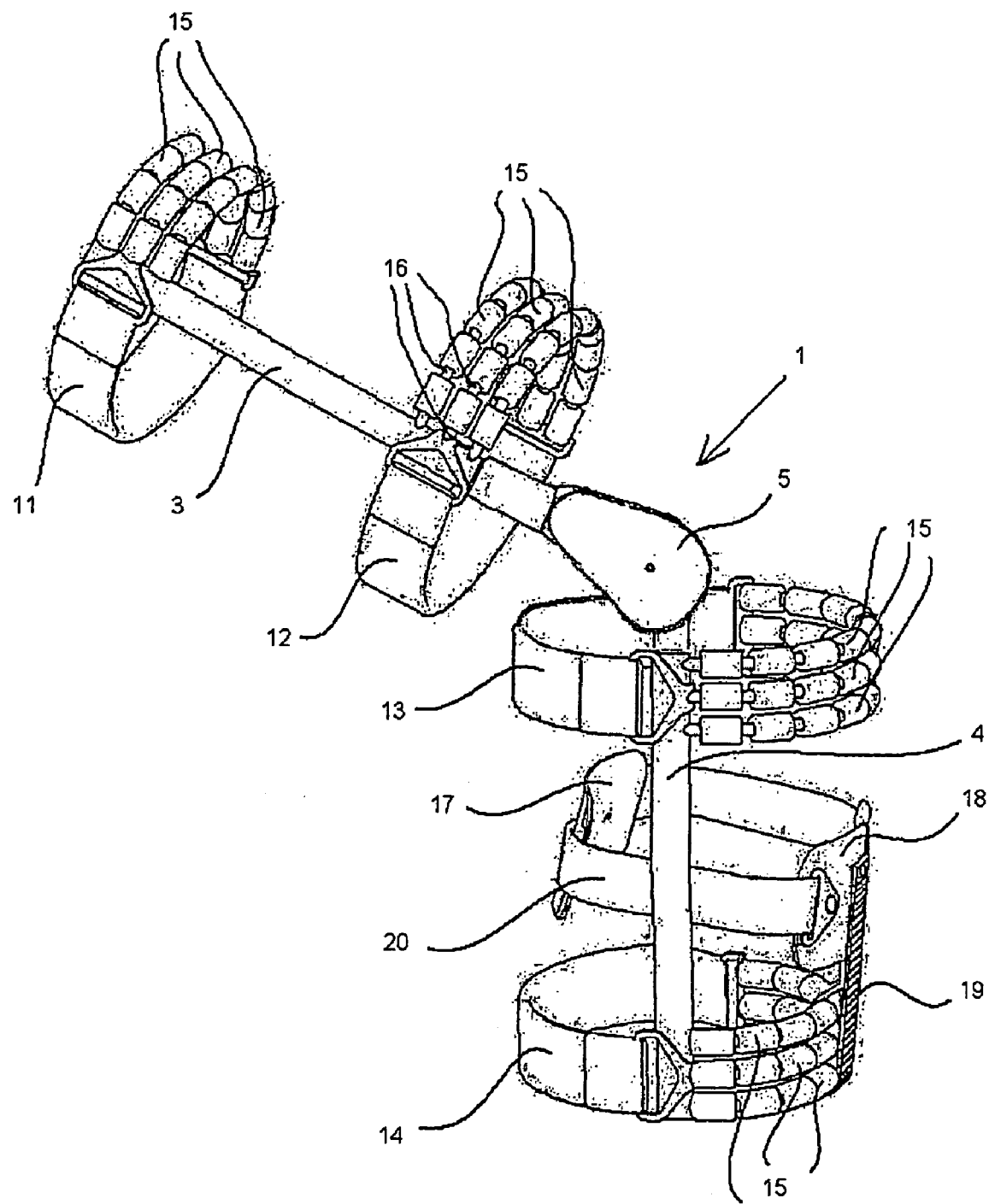
FIG. 3 is a perspective view of the orthosis in bent state.

Further situated in the region of the lower rod 4 is an additional flexible ring 20 with adjustable periphery. This ring has on its rear side a first pressure plate 17 and is provided on its front side with a second pressure plate 18 having on its underside a loop 19 of elastic strap material which is trained around the rollers 15 of lower ring 14 in the manner shown in FIG. 3.

The skin can move freely relative to the front side of rings 11, 12, 13, 14 since the rollers 15 can make a rolling movement in relation to the skin. The rings 11, 12, 13, 14 do not hereby move to any appreciable extent with the skin, at least in the region of rollers 15. Rollers 15 do not however impede the stated desirable displacement that occurs during bending and straightening of joints and hinges, while the fastening rings are moreover able to transfer the required forces between the limb parts and the fastening means, and thereby onto the device.

The extra ring 20 with loop 19 serves for a good positioning of the device in relation to the lower leg. Use is made for this purpose of a clamping of the device on the lower leg under the influence of a combination of the weight of the device and the forces on the device which occur for instance during movement of limb parts.

Figure 4:
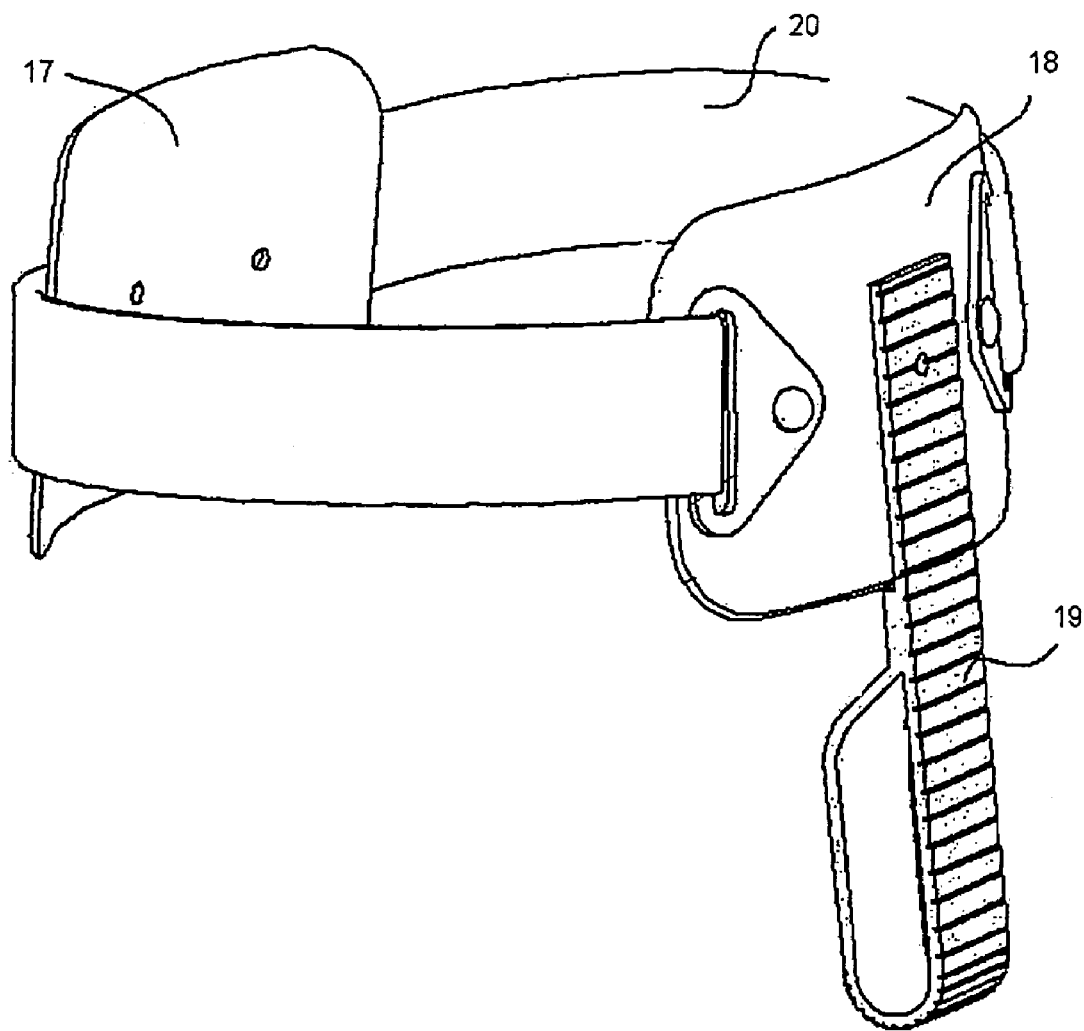
FIG. 4 is a perspective view of a component of the orthosis.
Figure 5:
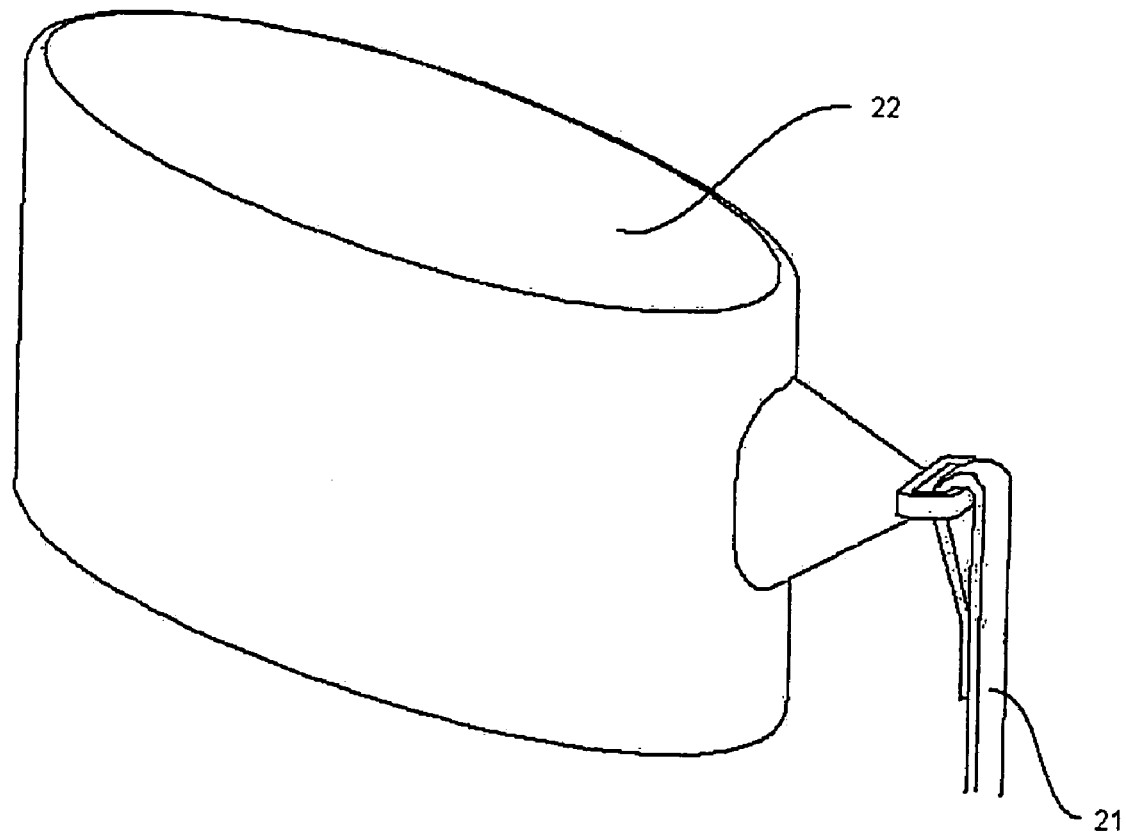
FIG. 5 is a perspective view of an alternative for a component as according to FIG. 4.

Because the additional ring 20 not provided with friction-reducing means is only arranged in the region of the lower leg rod 4, the clamping force is proportional to the force which device 1 exerts on ring 20, either through the direct transfer of forces as in the case of ring 20 according to FIG. 4, or through transfer of moments of force through a rigid annular structure 22 with a tensioning strap 21 arranged thereon of for instance elastic material as in FIG. 5. The advantage is that the clamping force varies as required and that it is not necessary to always apply a fixed clamping force which is always great enough to prevent undesirable shifting displacement of the device. Form and embodiment of rings 20, 22 respectively the optionally elastic tensioning straps or draw springs 19, 21 largely determine which forces are transferred from rings 20, 22 to device 1. The tensioners 19, 21 can be designed such that the forces resulting from the desired shifting displacements, for example as a result of the movement of the knee, remain small. A possible embodiment of the tensioners is thus an elastic strap or draw spring.

The invention is not limited to the drawn and described embodiments.

The invention claimed is:

1. An orthopedic device, in particular a prosthesis or an orthesis, for the purpose of replacing respectively supporting the function of at least one part of a human limb with a pivotable joint, for example a leg with a knee or an arm with an elbow, on either side of which joint there extend respective limb parts, such as a lower leg and an upper leg respectively a lower arm and an upper arm, which device comprises:

a structure comprising two substantially rigid parts, for instance two rods, which parts are coupled to each other by means of hinge means and each comprise fastening means for optional temporary fastening to a limb part, wherein a pivot axis of the hinge means extends at least more or less in the region and in the direction of the pivot axis zone of the relevant joint, said fastening means being at least partly provided with friction-reducing means on at least the side to be brought into contact with the relevant limb part, wherein the friction-reducing means comprise a number of freely rotatable elements.

2. The device as claimed in claim 1, wherein said structure is provided on only one side with hinge means and wherein said rotatable elements are selected from the group consisting of rollers and balls.

3. The device as claimed in claim 1, wherein the fastening means comprise divisible flexible rings with adjustable periphery.

4. The device as claimed in claim 1, wherein at least one additional ring with adjustable periphery, which ring is connected or can be connected to a structural part and is free of friction-reducing means.

5. The device as claimed in claim 4, wherein the additional ring is coupled or can be coupled to a ring provided with friction-reducing means by means of an optionally adjustable tensioner extending in longitudinal direction, for example a cord, a draw spring or an elastic strap.

6. The device as claimed in claim 1, wherein the device is a knee orthesis.

7. The device as claimed in claim 1, wherein the device is a knee-ankle-foot orthesis.

* * * * *